United States Patent [19]

Nappholz

[11] Patent Number: 5,609,610
[45] Date of Patent: Mar. 11, 1997

[54] DUAL CHAMBER PACEMAKER WITH AUTOMATIC ADAPTATION FOR INTRINSIC ATRIAL EVENTS

[75] Inventor: Tibor Nappholz, Englewood, Colo.

[73] Assignee: Telectronics Pacing Systems, Inc., Englewood, Colo.

[21] Appl. No.: 530,054

[22] Filed: Sep. 19, 1995

[51] Int. Cl.⁶ .................................................. A61N 1/365
[52] U.S. Cl. .................................. 607/9; 607/17; 607/25
[58] Field of Search .................................. 607/9, 14, 17, 607/25, 27; 128/697

[56] References Cited

U.S. PATENT DOCUMENTS

| | | |
|---|---|---|
| 4,554,921 | 11/1985 | Boute et al. . |
| 4,569,350 | 2/1986 | Mumford et al. ........................ 128/697 |
| 4,624,260 | 11/1986 | Baker, Jr. et al. ........................ 607/14 |
| 4,702,253 | 10/1987 | Nappholz et al. . |
| 4,802,483 | 2/1989 | Lindgren . |
| 5,074,308 | 12/1991 | Sholder et al. ........................ 607/27 X |
| 5,085,215 | 2/1992 | Nappholz et al. . |
| 5,103,820 | 4/1992 | Markowitz . |
| 5,123,412 | 6/1992 | Betzold . |
| 5,129,393 | 7/1992 | Brumwell . |
| 5,301,669 | 4/1994 | Duncan ........................................ 607/9 |
| 5,312,450 | 5/1994 | Markowitz ................................ 607/14 |

*Primary Examiner*—Jeffrey R. Jastrzab
*Attorney, Agent, or Firm*—Gottlieb, Rackman & Reisman

[57] ABSTRACT

In an implanted pacemaker three basic pacing intervals are established: an A-V delay, a PVARP and an alert interval. These three intervals together define an atrial-to atrial interval which is preferably a function of a metabolic indicated rate. The PVARP and alert interval are adaptively adjusted to optimize the PVARP for the patient without affecting the atrial-to-atrial interval.

13 Claims, 7 Drawing Sheets

DUAL CHAMBER PACEMAKER WITH AUTOMATIC ADAPTATION FOR INTRINSIC ATRIAL EVENTS

BACKGROUND OF THE INVENTION

A. Field of the Invention

This invention relates to dual chamber pacemakers, and more particularly to a mode of operation which automatically determines whether an intrinsic atrial event occurring prematurely is physiological and pathological, and adapts its operation accordingly.

B. Background of the Invention

Conventional pacemakers which employ the automatic mode switching in upper rate response may induce pacemaker mediated tachycardia after an atrial arrhythmia has been terminated, when switching from the VVI or VVIR mode to the DDD or DDDR mode. During the first cardiac cycle after the mode switch, the origin of the first A-sense is unknown. It Could be either of atrial origin, i.e., a P-wave, or a retrograde P-wave caused by the previous V-pace. Also, with a Wenckebach response the AV delay is prolonged and thus the atrium has a longer period in which to repolarize and thereby provide a retrograde pathway for conduction, which may permit pacemaker mediated tachycardia. In U.S. patent application Ser. No. 226,654, filed Apr. 17, 1994, now U.S. Pat. No. 5,441,523 by Tibor Nappholz, incorporated herein by reference, hereinafter the Nappholz application a forced synchrony function is provided which inserts an A-pace if it is required, and thereby the retrograde pathway is made refractory so that a pacemaker mediated tachycardia cannot be induced by retrograde conduction.

However, another problem with existing pacemakers is that with the continued variability of the patient's physiology even the forced synchrony approach disclosed in the Nappholz application may become ineffective. In addition there is the ever present possibility of extraneous noise precipitating pacemaker mediated tachycardia (PMT). More specifically, during the initialization of a prior art dual chamber system, the physician must use a compromise in selecting the PVARP (Post Ventricular Atrial Refractory Protection) interval. On one hand, the physician must allow a sufficiently fast synchronized atrial rate tracking. On the other hand the patient's heart must be protected from pacer mediated tachycardia. In the Nappholz application, this is accomplished by adjusting the PVARP interval in accordance with the metabolic indicated rate. This approach provides effective protection at low metabolic rates however, the protection is lessened at higher rates. Another disadvantage of this approach is that, in younger patients the onset of normal sinus rhythm could be very fast and could exceed the shortening effect of the metabolic rate on the PVARP interval, resulting in loss of synchrony and the possible induction of PMT.

OBJECTIVES AND SUMMARY OF THE INVENTION

An objective of this invention is to provide a dual chamber pacemaker with a forced synchrony function which constantly monitors where in the cardiac cycle atrial events occur, with automatic adjustments being made in the PVARP to accommodate the changes in conduction patterns and physiology.

A further objective is to provide an improved dual pacemaker wherein the length if the PVARP interval is automatically optimized thereby increasing the protection against PMT's, and decreasing the chance of correct atrial events hitting the PVARP.

Briefly, a pacemaker constructed in accordance with this invention includes means for sensing and pacing both the atrium and the ventricle. The ventricle and atrium are paced and sensed by these means in accordance with the following rules. The A—A intervals are partitioned into four windows or sections. The first section is the A-V delay. The second section is an atrial blanking period. The third section is the PVARP interval. The fourth and last section is the Alert period. The A—A interval is inversely proportional to the metabolic rate indicated rate. The various sections making up the A—A intervals may likewise changed with the metabolic indicated rate. If an atrial event occurs within the Alert period, then it is considered to be a P-wave of sinoatrial origin. All such events are followed by an appropriate A-V delay and a V-pace.

If the atrial event occurs before the Alert period, i.e. in the PVARP, it is considered to be a pathological event and forced synchrony is provided. Forced synchrony maintains a stable V—V interval by adjusting the A-V delay through an A-pace after the atrial relative refractory period.

There are two categories of atrial events which may occur outside the Alert window:

(i) An event which is early in the cardiac cycle such that the remainder of the VV interval is greater than the programmed maximum AV delay, which is usually 260 ms—In this case, an API and an AV delay are calculated, and an A-pace is provided at the end of the API. This provides the hemodynamic benefit of AV synchrony. This also makes the atrium and the AV node refractory to preclude a PMT.

(ii) An event which is late in the cardiac cycle such that the remainder of the VV interval is less than the programmed maximum AV delay—In this case, the remainder of the VV interval is completed by the required AV delay.

The calculation of the remainder of the VV interval is a constant process. Depending on the cardiac rhythm, VV interval may be determined from one of three sources:

(i) the "average atrial rate" [AAR] (usually over the last four cycles);

(ii) the sensor derived "metabolic indicated rate" [MIR] (e.g., minute volume); or (iii) the programmed minimum rate (in the absence of a sensor).

When switching between these sources, there is a gradual transition to avoid erratic ventricular rates.

Importantly, according to this invention, the heart is closely monitored after each excursion into the PVARP. If every transgression is followed sequentially by A-V prolongation and an increase in the MIR and if this change in the MIR is not transient then a physiological tachycardia is assumed and the demarcation between the Alert period and the PVARP, i.e., the duration of PVARP is decreased with a long time constant. In this manner, the A—A interval gradually and automatically adapts to the physiology of the patient. The decrease in PVARP is conversely monitored by the occurrence of PMTs. These are detected as described in U.S. Pat. No. 5,423,868, by T. Nappholz et al., entitled, A DUAL CHAMBER PACEMAKER WHICH DETECTS, CONFIRMS AND TERMINATES PMT, incorporated herein by reference. PMTs indicate the excessive shortening of PVARP and the need for PVARP lengthening.

BRIEF DESCRIPTION OF THE DRAWINGS

Further objects, features and advantages of the invention will become apparent upon consideration of the following description, taken in conjunction with the accompanying drawing, in which.

DETAILED DESCRIPTION OF THE INVENTION

Figure 1:
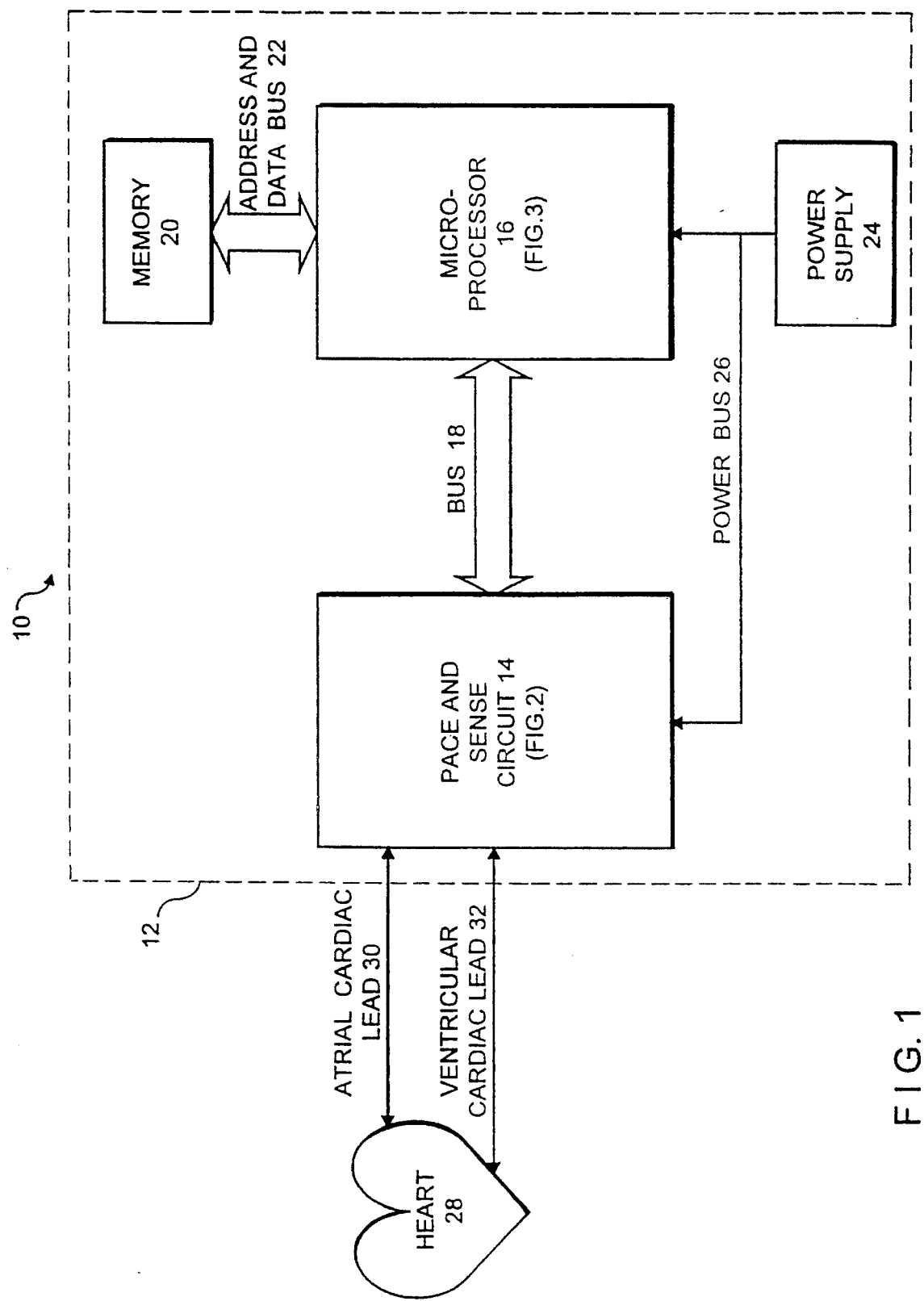
FIG. 1 shows a block diagram of a pacemaker constructed in accordance with this invention.

Referring now to FIG. 1, a pacemaker 10 constructed in accordance with this invention includes an implantable housing 12. The housing holds a pace and sense circuit 14, described in more detail in FIG. 2, and a micro-processor 16, described in more detail in FIG. 3. The pace and sense circuit 14 and the microprocessor 16 are interconnected by a bus 18 for exchanging data, as well as communication and control signals. The pacemaker 10 further includes a memory 20 connected to the microprocessor 16 by a data and address bus 22, and a power supply 24 providing power to the various components of pacemaker 10 via power bus 26.

Once implanted, the pacemaker 10 is connected to a patient's heart 28 by two leads 30, 32. Preferably, these leads 30, 32 are bi-polar leads with lead 30 being connected to the atrial chamber of the heart, and lead 32 being connected to the ventricular chamber. Therefore leads 30 and 32 are known as the atrial cardiac lead and the ventricular cardiac lead, respectively. It should be understood that the arrangement of the pacemaker 10 and leads 30 and 32 do not form a part of this invention. Other arrangements may be used as well, using other types of leads including tri-polar leads, unipolar leads and so on.

Figure 2:
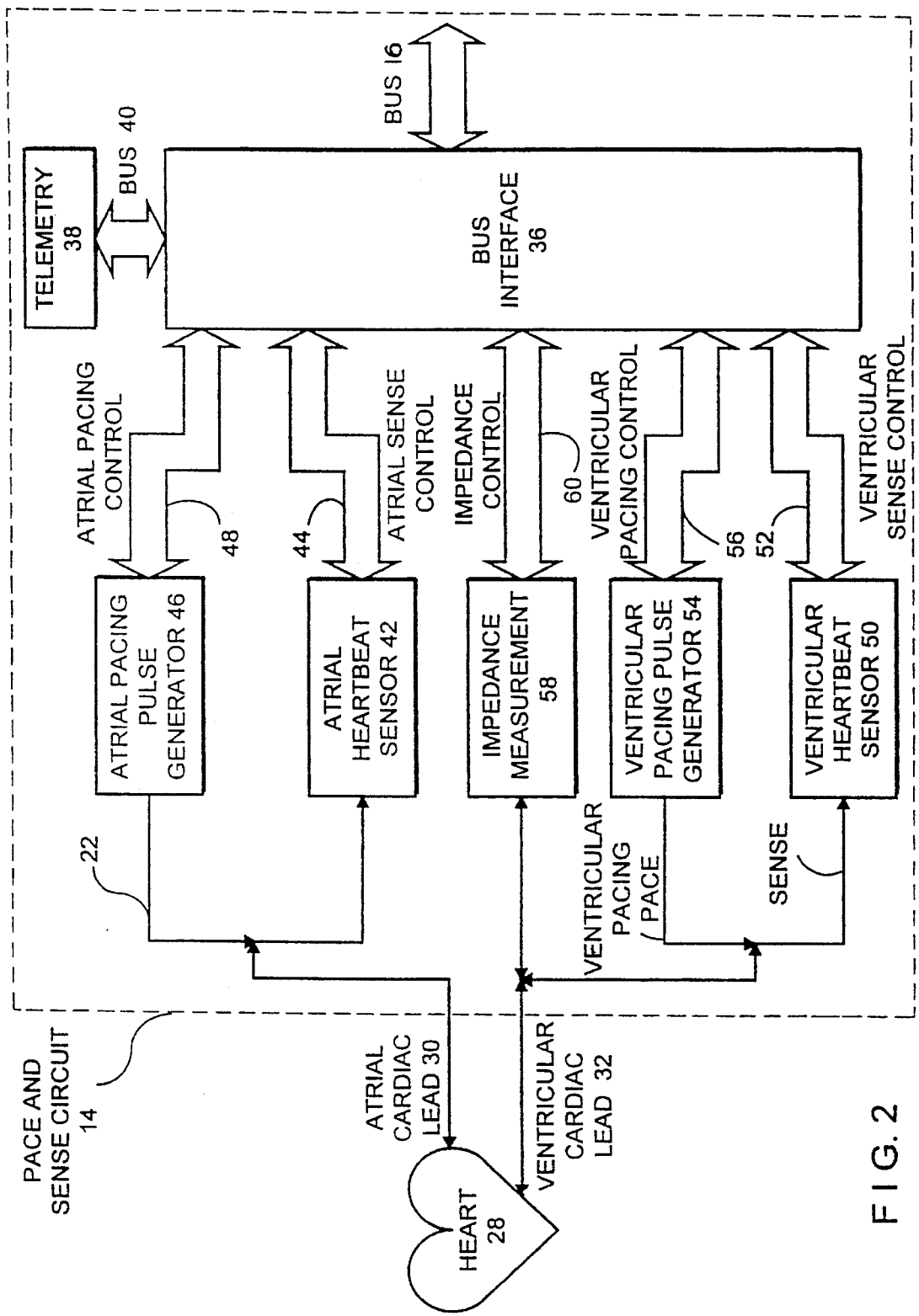
FIG. 2 shows a block diagram for the pace and sense circuit for the pacemaker of FIG. 1.

Referring now to FIG. 2, the pace and sense control circuit 14 includes a bus interface 36, a telemetry circuit 38 and various other sensing and control circuits for sensing the status of the chambers of heart 28 and to provide appropriate pacing signals thereto. The bus interface 36 provides interfacing with microprocessor 16 via bus 18. The telemetry circuit 38 provides communication with the outside world by, for example, RF, or inductive coupling. Signals with the telemetry circuit are exchanged via telemetering bus 40.

More specifically, signals from the atrium are sensed through lead 30 by the atrial heartbeat sensor 42. This sensor 42 is controlled by the atrial sense control bus 44. Atrial pacing pulses are generated for lead 30 by atrial pacing pulse generator 46. This generator is controlled by the atrial pacing control bus 48. Similarly, the ventricular chamber is sensed through lead 32 by ventricular heartbeat sensor 50, which is controlled by a ventricular sense control bus 52. Pacing pulses for the ventricular chamber are generated by the ventricular pacing pulse generator 54, controlled by the ventricular pacing control bus 56.

In addition, the impedance of the heart tissues is measured through one of the cardiac leads, such as lead 32, by impedance measurement circuit 58. This circuit is controlled by impedance control bus 60. All the control buses are interconnected between their respective circuits and the bus interface 36 to provide two way communication with the microprocessor 16.

Figure 3:
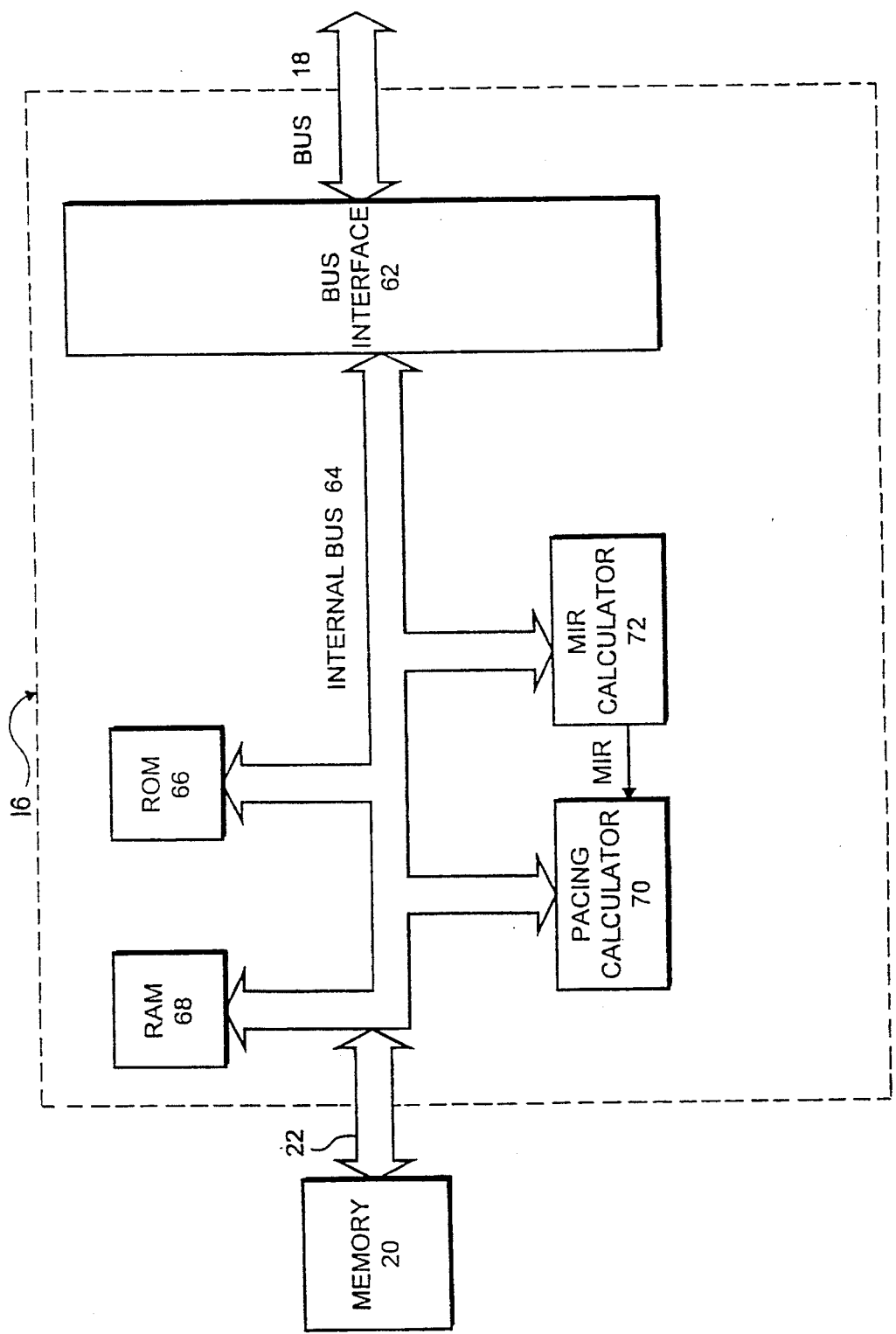
FIG. 3 shows a block diagram for the microprocessor of FIG. 1.

Referring now to FIG. 3, the microprocessor 16 includes a bus interface circuit 62 for interfacing with bus 18, and an internal bus 64 interconnecting the various components of the microprocessor 16. The microprocessor 16 further includes a read only memory (ROM) 66 used for storing programming information, a random access memory (RAM) 68 used as a scratch pad, a pacing calculator 70 and a metabolic indicated rate (MIR) calculator 72.

Except as noted below, the operation of the pacemaker 10 illustrated in FIGS. 1–3 is described in Nappholz application Ser. No. 226,654 now U.S. Pat. No. 5,441,523. Briefly, the impedance of the tissues of the heart 28 is measured by impedance measurement circuit 58 at regular intervals. These sequential measurements are transmitted via control bus 60, bus 18 and internal bus 64 (through the interface circuits 36 and 62) to the MIR calculator 72. This calculator 72 converts these impedance measurements into a minute volume corresponding to the patient's metabolic oxygen demand. Such a calculator is disclosed for example in commonly assigned U.S. Pat. No. 4,901,725, incorporated herein by reference. Of course, any other physiological rate responsive parameter could be used for the purposes of this application. This minute volume is in turn transformed into a metabolic indicated rate (MIR) and transmitted to the pacing calculator 70. The pacing calculator 70 also receives information regarding the sensing and/or pacing of the atrial and/or ventricular chambers of heart 28 through the respective sensors 42, 50. Based on the received information, the calculator 70 generates pacing control signals for pacing the heart in a particular mode. These control signals are transmitted to the pacing pulse generators 46 and 54 which in response generate appropriate pacing pulses to the ventricle and atrium as described above.

Figure 4:
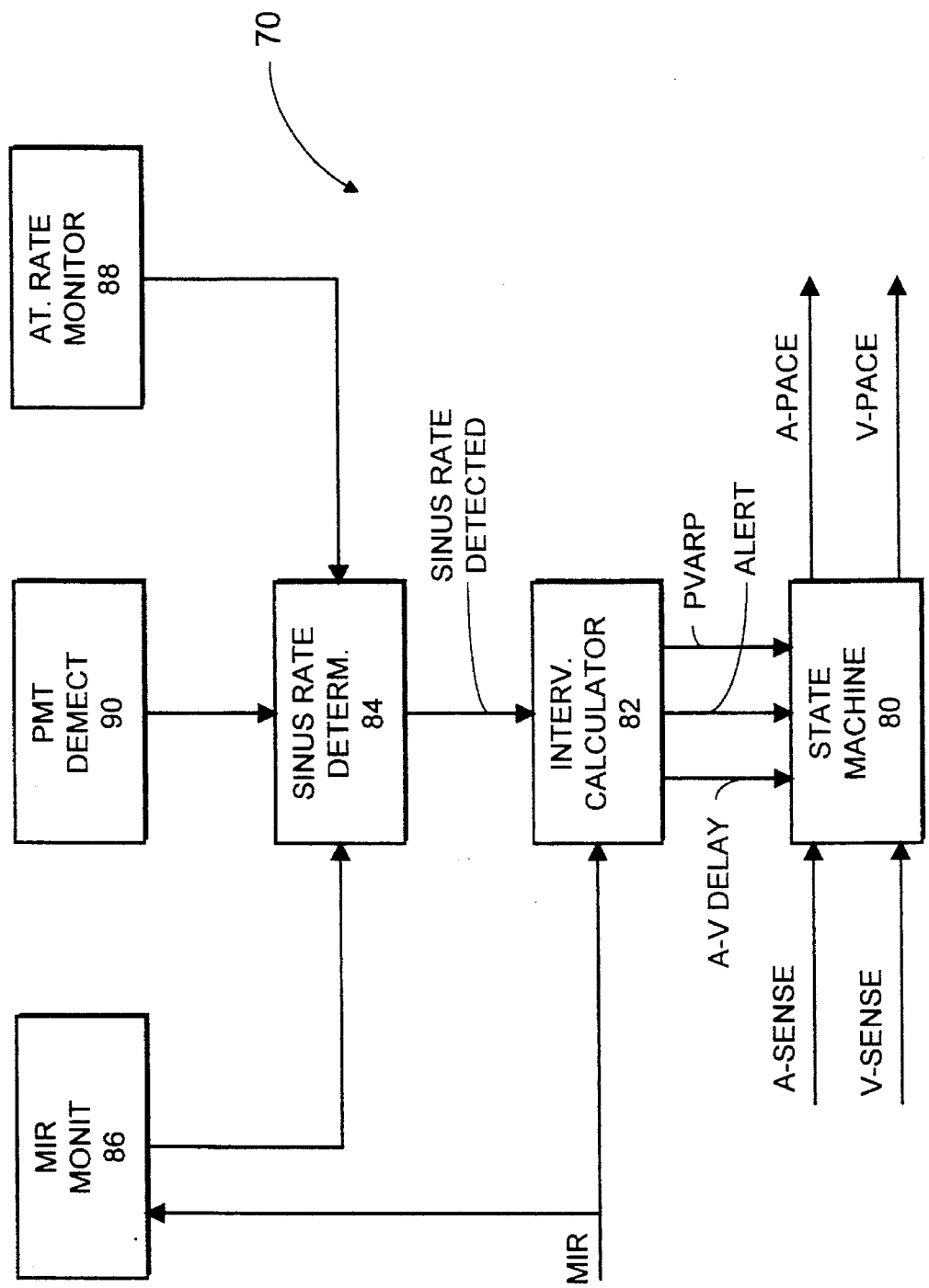
FIG. 4 shows a block diagram for an interval calculator for FIG. 3.
Figure 5:
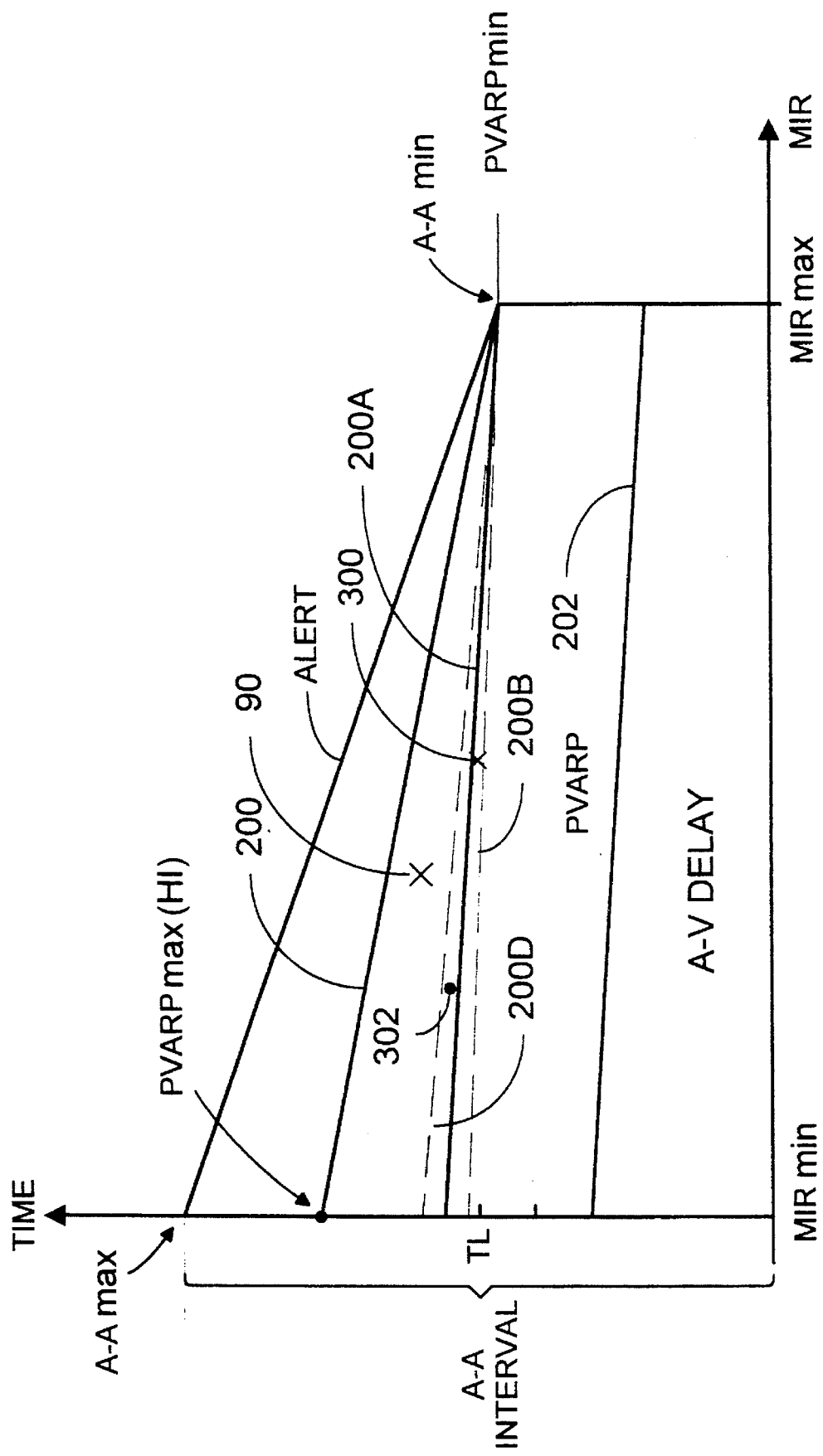
FIG. 5 shows a graph for the A—A interval and its components.
Figure 6:
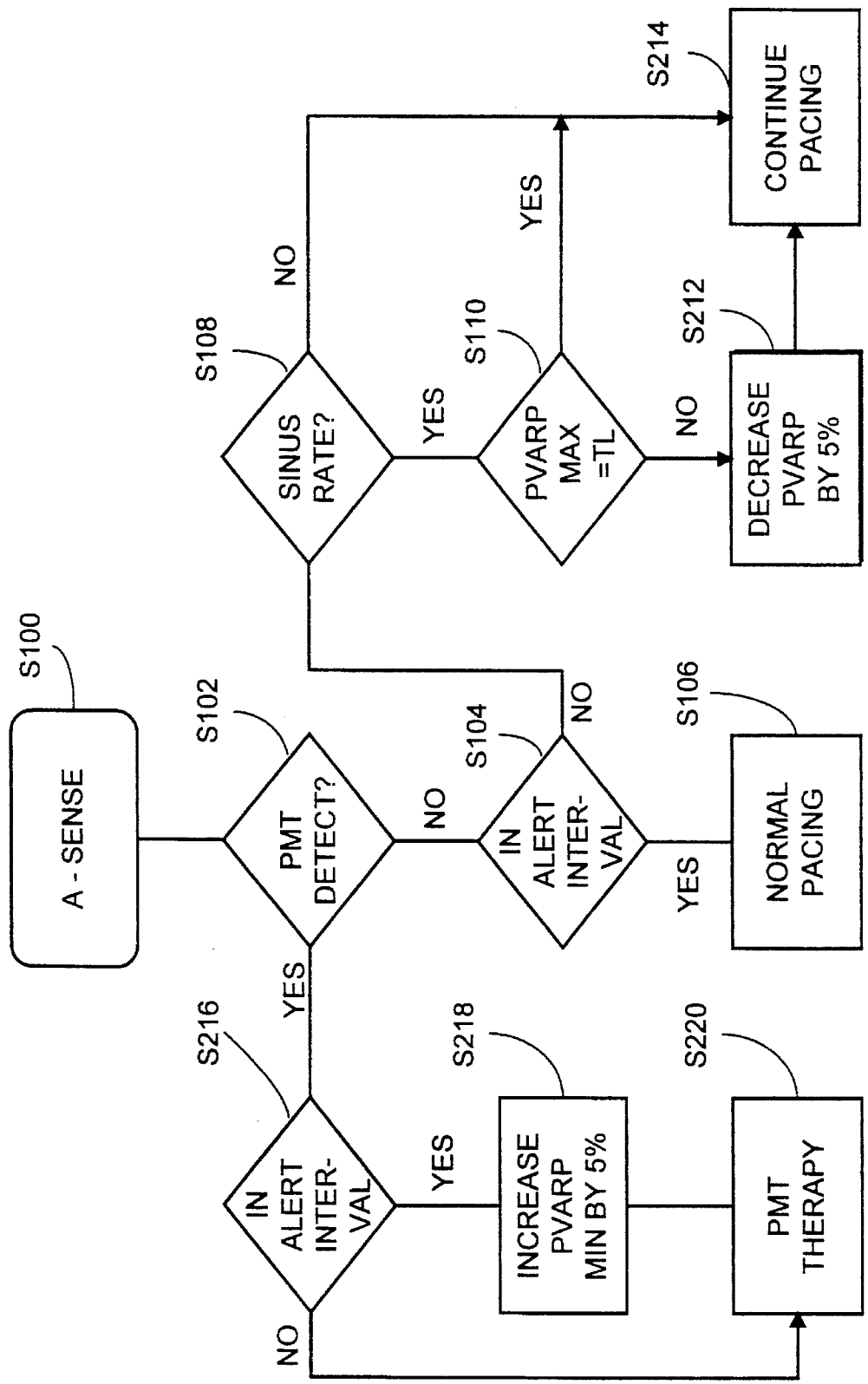
FIG. 6 shows a flow chart for the interval calculator of FIG. 4.
Figure 7:
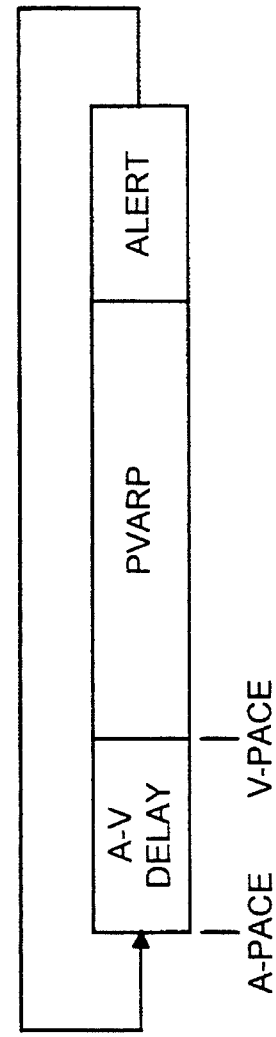

Details of the pacing calculator are shown in FIG. 4. This calculator 70 includes a state machine 80, an interval calculator 82 and a sinus rate determinator 84. The normal operation of the pacing calculator 70 is shown in FIGS. 5, 6 and 7. In FIG. 5, the vertical axis represents time and it illustrates how a typical A—A (atrial-to-atrial) interval is partitioned in the calculator 70. More specifically, as shown in FIG. 7, this interval is partitioned into three periods. The first period immediately following an A-pace or an A-sense, is the A-V delay. The A-V delay is followed by a PVARP interval (Post Ventricular Atrial Refractory Period). (The PVARP is normally preceded by an atrial blanking period, which has been omitted in the Figure for the sake of clarity). The PVARP may also include toward its end a fixed or variable length API (Atrial Protection interval), which has also been omitted. The last period of interest is the Alert period. Initially the demarcation between the PVARP and Alert intervals is line 200 obtained as described below.

Referring now to FIG. 5, the vertical axis shows the A—A interval.

The horizontal axis in FIG. 5 represents the MIR min parameter. The lowest value of MIR, corresponds to the minimum or rest pacing rate for the heart. As the MIR parameter increases, the A—A interval decreases linearly from a maximum value A—A MAX towards a minimum value A—A MIN corresponding to the maximum pacing rate MIR max. The three periods making up the A—A interval also similarly decrease with increased MIR, with the Alert period preferably decreasing to zero as shown.

Figure 8:
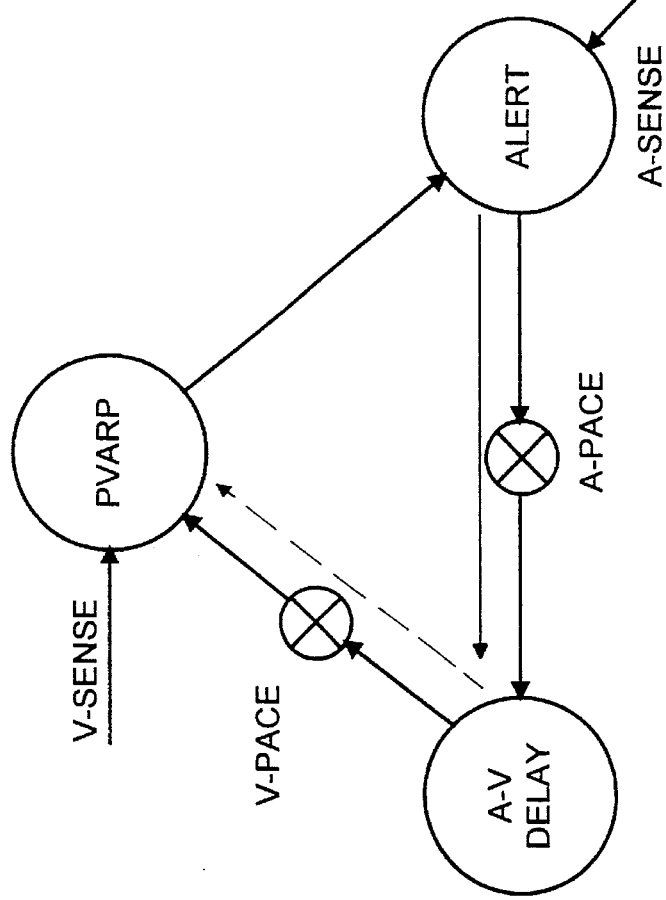
FIGS. 7 and 8 shows the partitioning of the A—A interval and the corresponding state diagram.

The lengths or durations of these three periods are determined by the interval calculator 70 FIG. 4 and fed as operational constants to the state machine 80. The state machine 80 also receives the A-sense and the V-sense signals as inputs. The operation of the state machine is illustrated in FIGS. 7 and 8. As seen in these Figures, normally an atrial event (A-sense) is sensed in the Alert period initiates the A—V delay. If there is no A-sense signal sensed at the end of the Alert period than the state machine-80 issues an A-pace. Either an A-sense or an A-pace result in the A-V delay. If no ventricular event is sensed in the A-V delay then at the end of this period a V-Pace is issued. A V-sense or V-pace initiate the PVARP period. The PVARP is followed by the Alert period.

The lengths or durations of the maximum and minimum values of the A—A interval and its components are programming parameters which may be set by the physician. Historically the physician sets the maximum value of the PVARP (PVARP max (HI)) to the maximum levels permissible by the patients cardiac condition. Points PVARP max (HI) and A—A min define in FIG. 5 line 200 which initially separates PVARP from ALERT. The objective of this invention is to eliminate the need for the physician to consider programming PVARP. As previously mentioned, any setting may not be ideal for certain patients, such as relatively young and physically active patients. In these situations, an A-sense may occur in the PVARP as indicated in FIG. 5 at 90. This type of event may be either pathological or physiological. If it is pathological, then it can be handled by using the forced synchrony technique discussed in the Nappholz application. However, if the occurrence is physiological, that is, it is due to sinus rhythm, then the PVARP period is too long and should be recorded so that PVARP may be gradually adjusted.

For this purpose, the calculator 70 includes a sinus rate determinator 84. This determinator makes a determination on whether an A-sense signal is caused by a sinus rate or not. If a sinus rate detected, the determinator sends an appropriate signal to the interval calculator. In response, the calculator 82 reduces the PVARP max by an incremental amount such as for example, 5%. Since the minimum value of the A—A interval remains unchanged, the result of this last operation is to move the demarcation line between PVARP and the Alert period slightly downward.

The sinus rate determination may be performed using various criteria. One criteria is to monitor the MIR signal using MIR monitor 86. This involves a "look back corrolator". This detection scheme tracks the changes in MIR with respect to changes in atrial rate. If the MIR tracks the average atrial rate (even with a time delay), the atrial response is assumed to be physiologically induced.

Another method of determining sinus rate is to monitor the intrinsic atrial heart beat using atrial rate detection 88. A gradual increase in atrial rate prior to the suspect A-sense is also indication of a sinus rate. This is the "onset criteria" used in defibrillators.

Finally, the cardiac functions may also be monitored to determine, if heart is undergoing a PMT (Pacemaker Mediated Tachycardia) condition using a PMT detector 90. Obviously a PMT condition indicates a pathological condition rather than a sinus rate. A PMT detector is disclosed in commonly assigned U.S. Pat. No. 5,423,868 mentioned above.

The optimum PVARP duration is the shortest duration which does not result in PMT. However, an A-sense falling in the Alert interval during PMT is indicative of a PVARP which is too short. Therefore, under these conditions the interval calculator increments-the value of PVARP max by 5% thereby shifting the demarcation line upwards.

In this manner, the operation of the pacing calculator is adaptively optimized for the proper PVARP to a position such as the one indicated by line 200A.

Details of the operation of the calculator 70 are shown in the flow chart of FIG. 6. The operation of the calculator starts with an A-sense signal, step S100. In step S102 a determination is made of whether the patient's heart is in a PMT condition. The determination of step S102 may be performed for each atrial event sensed in step S100. Alternatively, an X of 7 approach could be incorporated into steps S100 and S102 wherein X atrial events of a total of 7 atrial events must be related to PMT in an affirmative determination. For example, if 4 out of 6 or 6 out of 10 consecutive atrial events can be classified as being indicative of PMT, then the determination of step S102 is "yes".

If the determination in step S102 is 'NO' than in step S104, a determination is made as to whether the A-sense is within the Alert interval. If in step S104 it is determined that the A-sense is in the Alert interval than in step S106 the normal pacing sequence is provided as shown in FIG. 7.

If in step S104 it is determined that the A-sense is suspect because it is outside the Alert interval, then in step S108 a determination is made as to whether the heart beat is occurring at a sinus rate. As previously mentioned, this determination can be made using one or more of three different techniques. If in step S108 it is determined that the atrium is beating at a sinus rate then in step S110 a determination is made as to whether the PVARP max level has reached a preselected minimum threshold level TL. The PVARP max will not be decremented below this level. If in step S110 the determination is negative, then in step S112 the PVARP max level is decremented by a preset value, such as for example 5% . Otherwise the normal pacing sequence is continued in step S214.

Going back to step S102, if a PMT condition is detected, then PMT therapy is provided in step S214. Next, again in step S216 a determination is made as to whether the A-sense is in the Alert interval. If this determination is positive, this is an indication that the PVARP duration is too low. Therefore in step S218 the PVARP max is increased by a preselected incremental value such as 5% . Next, the subroutine is terminated in step S200. PMT therapy may be applied. If the determination in step S216 is negative, then step S218 is skipped.

The results of the procedure of FIG. 6. Is shown in FIG. 5. In this figure the attending physician sets the PVARP max (HI) and PVARP min levels and the other parameters. These levels of PVARP (max or min) will be set as a result of maximum allowed ventricular rate (max rate) set by the physician, where max rate =60/(AV+PVARP (min)). As a result, the A—A interval is partitioned into the three time dependent intervals: A-V delay, PVARP and Alert by lines 202 and 200. The minimum allowable level for PVARP max is shown in FIG. 5 as TL. At a certain time after the pacemaker has been put in service, the PVARP max has been adaptively adjusted by the process of FIG. 6 resulting in demarcation line 200A. At this time an A-sense sequence is received indicated in FIG. 5 by point 300. After a determination is made that this A-sense sequence point 300 has occurred under sinus rate conditions, the demarcation line is adjusted by reducing it slightly, as indicated by line 200B.

Suppose instead of point 300, another A-sense sequence is received, indicated by point 302 during a PMT condition.

Since point 302 is in the Alert interval, the demarcation line is shifted upward slightly resulting in line 200D.

Although the invention has been described with reference to several particular embodiments, it is to be understood that these embodiments are merely illustrative of the application of the principles of the invention. Accordingly, the embodiments described in particular should be considered exemplary, not limiting, with respect to the following claims.

I claim:

1. A pacemaker comprising:

atrial sensing means for sensing atrial activity;

classifying means for determining if said atrial activity is pathological or physiological;

first delay means for establishing an A-V delay in response to said atrial activity;

ventricular sensing means for sensing ventricular activity;

ventricular pacing means for generating ventricular pacing pulses at the end of said A-V delay in the absence of ventricular activity;

second delay means for establishing a PVARP after one said ventricular activity sensing and pacing;

third delay means for establishing an alert interval at the end of said PVARP; and means for adjusting the length of said PVARP and alert interval in response to sensing atrial activity for optimizing the PVARP without changing the total duration of said PVARP and said alert intervals.

2. The pacemaker of claim 1 further comprising means for determining a metabolic indicated rate for said ventricular pacing, and wherein said first, second and third delay means define an A—A (atrial-to atrial interval), said A—A interval being a function of said metabolic indicated rate and wherein said A—A interval remains unaffected while PVARP and alert intervals are adjusted by said means for adjusting the length of said PVARP.

3. The pacemaker of claim 1 wherein said adjusting means includes means for increasing said PVARP when a sinus atrial events are sensed in said alert interval.

4. The pacemaker of claim 1 wherein said classifying means includes means for determining if an atrial event is due to a pacemaker mediated tachycardia (PMT).

5. The pacemaker of claim 4 wherein said adjusting means increases said PVARP in the presence of PMT.

6. An implantable pacemaker for implantation in the body of a patient, said pacemaker comprising:

sensor circuitry for sensing intrinsic atrial and ventricular events in the heart of a patient;

pacing circuitry for generating atrial and ventricular pacing pulses in the absence of said intrinsic atrial and ventricular events respectively;

rate deriving circuitry for deriving a metabolic indicated rate for defining a ventricular pacing rate;

a timer for establishing an A-V delay, a PVARP, and an alert interval to define an atrial-to-atrial interval based on said atrial and ventricular intrinsic events and/or said atrial and ventricular pacing, said atrial-to-atrial interval being varied as a function of said metabolic indicated rate;

classifying circuitry for classifying an atrial event sensed by said sensing circuitry as one of a pathological and physiological event; and adjusting circuitry for adjusting said PVARP and said alert interval based on said classifying circuitry without changing said atrial-to-atrial interval to optimize said PVARP.

7. The pacemaker of claim 6 wherein said adjusting circuitry includes determining circuitry for determining whether an atrial event sensed in said alert interval is a sinus event, and wherein said adjusting circuitry is adapted to increase said PVARP in response to said sinus event.

8. The pacemaker of claim 6 further comprising PMT sensing circuitry for sensing pacemaker mediated tachycardia (PMT) and wherein said adjusting circuitry is adapted to decrease said PVARP in response to said PMT.

9. The pacemaker of claim 8 wherein said PVARP is decreased when PMT is sensed in said PVARP.

10. A method of operating a pacemaker having sensors for sensing atrial and ventricular events and pacing circuitry for applying at least ventricular pacing pulses, rate response circuitry for generating a pacing rate for said ventricular pacing pulses at a pacing interval in accordance with a metabolic parameter, said method comprising the steps of:

establishing an A-V interval, a PVARP and an alert interval, the sum of said intervals being equal to said pacing interval;

initiating said A-V interval in response either to an intrinsic atrial event, or to an atrial pacing pulse;

at the end of said A-V interval determining if a ventricular intrinsic event has occurred;

generating a ventricular pacing pulse in the absence of a ventricular intrinsic event;

sensing an atrial event in said PVARP or said alert interval;

increasing said PVARP if an atrial event is sensed in said alert interval without changing said pacing interval; and decreasing said PVARP if said atrial event is sensed in said PVARP without changing said pacing interval to thereby optimize said PVARP.

11. The method of claim 10 wherein said PVARP is increased if a sinus atrial event is sensed in said alert interval.

12. The method of claim 10 wherein said PVARP is increased if a pathological atrial event is sensed in said PVARP.

13. The method of claim 12 wherein said pathological event is a pacemaker mediated tachycardia.

* * * * *